(12) United States Patent
Luo et al.

(10) Patent No.: US 9,371,364 B2
(45) Date of Patent: Jun. 21, 2016

(54) DUAL-TARGETED THERAPEUTIC PEPTIDE FOR NASOPHARYNGEAL CARCINOMA, NANOPARTICLES CARRYING SAME AND USES THEREOF

(71) Applicant: HUAZHONG UNIVERSITY OF SCIENCE AND TECHNOLOGY, Wuhan, Hubei (CN)

(72) Inventors: Qingming Luo, Wuhan (CN); Zhihong Zhang, Wuhan (CN); Haiming Luo, Wuhan (CN)

(73) Assignee: HUAZHONG UNIVERSITY OF SCIENCE AND TECHNOLOGY, Wuhan, Hubei (CN)

( * ) Notice: Subject to any disclaimer, the term of this patent is extended or adjusted under 35 U.S.C. 154(b) by 0 days.

(21) Appl. No.: 14/406,399

(22) PCT Filed: Jun. 7, 2013

(86) PCT No.: PCT/CN2013/000680
§ 371 (c)(1),
(2) Date: Dec. 8, 2014

(87) PCT Pub. No.: WO2013/181934
PCT Pub. Date: Dec. 12, 2013

(65) Prior Publication Data
US 2015/0344525 A1    Dec. 3, 2015

(30) Foreign Application Priority Data
Jun. 7, 2012 (CN) .......................... 2012 1 0185089

(51) Int. Cl.
| | | |
|---|---|---|
| A61K 38/16 | (2006.01) |
| C07K 14/00 | (2006.01) |
| C07K 7/08 | (2006.01) |
| A61K 9/51 | (2006.01) |
| A61K 31/12 | (2006.01) |
| A61K 31/337 | (2006.01) |
| C07K 14/47 | (2006.01) |
| A61K 47/48 | (2006.01) |
| A61K 49/00 | (2006.01) |
| A61K 38/10 | (2006.01) |
| A61K 47/42 | (2006.01) |

(52) U.S. Cl.
CPC ................ *C07K 7/08* (2013.01); *A61K 9/5123* (2013.01); *A61K 9/5169* (2013.01); *A61K 31/12* (2013.01); *A61K 31/337* (2013.01); *A61K 38/16* (2013.01); *A61K 47/48215* (2013.01); *A61K 47/48238* (2013.01); *A61K 47/48884* (2013.01); *A61K 49/0093* (2013.01); *C07K 14/4747* (2013.01); *C07K 14/4748* (2013.01); *A61K 38/10* (2013.01); *A61K 47/42* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 7,238,665 B2 * | 7/2007 | Wu ...................... | A61K 9/1271 |
| | | | 424/450 |
| 2009/0163408 A1 | 6/2009 | Fogelman et al. | |

FOREIGN PATENT DOCUMENTS

| | | | | |
|---|---|---|---|---|
| CN | 101876658 A | 11/2010 | | |
| CN | 102027019 A | 4/2011 | | |
| CN | 102766215 A | 11/2012 | | |
| EP | 2860193 A1 * | 4/2015 | ............ A61K 38/16 |
| WO | 2009073984 A | 6/2009 | | |

OTHER PUBLICATIONS

Zhang, et al., "Biomimetic Nanocarrier for Direct Cytosolic Drug Delivery", Angew. Chem. Int. Ed., Oct. 28, 2009, vol. 48, pp. 9171-9175.
Luo, et al., "Tetrameric far-red fluorescent protein as a scaffold to assemble an octavalent peptide nanoprobe for enhanced tumor targeting and intracellular uptake in vivo", The Faseb Journal, Feb. 24, 2011, vol. 25, pp. 1865-1873.
Luo, et al., "Vector Construction, Protein Expression and Purification of NAP1", Journal of Beijing Normal University (Natural Science), Oct. 31, 2007, vol. 43, No. 5, pp. 538-542.
International Search Report issued in corresponding application No. PCT/CN2013/000680 on Sep. 5, 2013.

* cited by examiner

*Primary Examiner* — Jeffrey E Russel
(74) *Attorney, Agent, or Firm* — Carter, DeLuca, Farrell & Schmidt, LLP

(57) ABSTRACT

Disclosed is a dual-targeted therapeutic peptide for nasopharyngeal carcinoma formed by covalently linking a targeted therapeutic peptide for nasopharyngeal carcinoma, a peptide linker and a targeted therapeutic peptide with an α-helical structure for nasopharyngeal carcinoma. Also disclosed is a nanoparticle containing the peptide. The peptide and the nanoparticle can be used to treat nasopharyngeal carcinoma.

9 Claims, 14 Drawing Sheets

DUAL-TARGETED THERAPEUTIC PEPTIDE FOR NASOPHARYNGEAL CARCINOMA, NANOPARTICLES CARRYING SAME AND USES THEREOF

TECHNICAL FIELD

The invention belongs to the field of bioscience and drug carriers, and in particular, relates to a dual-targeted therapeutic peptide for nasopharyngeal carcinoma, nanoparticles carrying the same and uses thereof.

BACKGROUND OF THE DISCLOSURE

Nasopharyngeal carcinoma, a highly malignant tumor originated from nasopharyngeal epithelium, is very easy to invade the base of skull and other important structures, and its cervical lymph node metastasis and distant metastasis may occur earlier. Nasopharyngeal carcinoma is hard to be treated by surgery since it has high malignancy with a special pathogenic site. Therefore, nasopharyngeal carcinoma is clinically treated mainly by radiotherapy in combination with systemic chemotherapy. However, the traditional radiotherapy and chemotherapy have serious toxic and side effects, and the radiotherapy only applies to the primary tumor and its sentinel lymph node metastasis, but not to its distant metastasis. The five-year survival rate for nasopharyngeal carcinoma patients fluctuates around 60% due to limitation in the therapeutic method.

Monoclonal antibody drugs have shown a good prospect for clinical application in tumor therapy. A conjugate formed by a monoclonal antibody with a radionuclide, a drug or a toxin showed a targeting specific lethal role on tumor cell. In addition, some monoclonal antibodies specific for tumor markers themselves have significant antitumor effects. For example, Herceptin, an antibody to epidermal growth factor HER-2/neu of tumor cell, has achieved a good curative effect as a targeting drug for HER-2 positive metastatic breast cancer. However, monoclonal antibody still has several limitations in practical clinic application. It has a problem of immunogenicity, since most of monoclonal antibody drugs for clinical study are prepared by using mice. It does not have a good treatment effect on large volume of solid tumor due to its large molecular weight and low penetration into tumor. It has an extremely high production cost since the tumor treatment requires a large amount of antibody with high purity. The inhibition or killing of tumor cells which express a certain receptor only by using a monoclonal antibody does not mean a cure of tumor because of the heterogeneity of the tumor cells. Thus, it is difficult to achieve a desired effect for the treatment of nasopharyngeal carcinoma with high grade of malignancy only by using a monoclonal antibody as the targeting molecule.

Peptide, as a specific ligand to the molecule of a tumor marker, is the focus of researcher's attention. Peptide has advantages of small size, good tissue penetrability, low immunogenicity and low cost, compared with the monoclonal antibodies, and may overcome the defects of antibody preparation to a large extent. However, the in vivo application of targeting peptides is limited due to its relatively weak affinity to tumor and short half-life. Multivalent strategies based on nanotechnology can significantly prolong the effective circulation time of targeting peptides in vivo, and greatly improve its affinity for binding with a specific receptor, so as to achieve the purpose of significantly enhancing the biological effect of the peptide.

For this reason, an octavalent peptide fluorescent nanoprobe based on tetramer far-red fluorescent protein was prepared by using a method for constructing a peptide fluorescent probe having multivalent and nanoscale effects found in our preliminary work. The tumor-targeting property and the biological anti-tumor effect of a peptide can be rapidly and accurately screened and identified by using the method. However, the clinical use of the far-red fluorescent protein is limited by its immunogenicity, because the far-red fluorescent protein is a foreign protein. Therefore, there is an urgent need to develop a nano-carrier capable of effectively transporting the targeted peptide without affecting its targeting property and therapeutic effect.

Nasopharyngeal carcinoma is a complex disease gradually developed from a multi-step interaction involving factors such as environmental factors and genetic genes of host. Clinical studies on the combined treatment with radiotherapy and adjuvant chemotherapy showed that a variety of anticancer drugs, either alone or in combination, have certain curative effect on nasopharyngeal carcinoma which is relatively sensitive to chemotherapy. The main water-soluble chemotherapeutic agents, such as cisplatin and 5-fluorouracil (5-FU), can significantly improve the prognosis of the patients. But regardless of alone or in combination, intravenously administered cisplatin and 5-FU have disadvantages of a short half-life and lack of selection, thereby increasing its toxic and side effects. Curcumin and paclitaxel are two kinds of representative anti-cancer herbal medicines. Curcumin, having many pharmacological effects, is a phenolic pigment extracted from the rhizome of *Curcuma longa*, a herbaceous plant. It is confirmed from many studies that curcumin can inhibit the growth of various tumor cells, and enhance the recruitment of NK cells in tumor microenvironment, thereby improving the body's immunity. Paclitaxel has been used in the treatment of advanced nasopharyngeal carcinoma, since it was first approved by FDA of US to enter into the clinic treatment of ovarian cancer in 1992. It has been found that paclitaxel can also enhance the recruitment of NK cells in tumor microenvironment and activate antigen presenting ability of dendritic cells, so as to enhance the immune responses against tumor cells. Because both curcumin and paclitaxel are fat-soluble drugs, they are difficult to be directly taken up by tumor tissue cells via passive transportation, and have highly toxic and side effects in a vein, and thus have poor clinic applications currently. So far, a targeted therapeutic nano-drug for nasopharyngeal carcinoma has not been reported in China.

Nano-carrier is an effective means for targeted delivery of an imaging contrast agents or a drug to tumor cells to achieve specific imaging diagnosis and targeted treatment of tumor. A high-density lipoprotein-like peptide-lipid nanoparticle has been invented (International Publication Number: WO2009073984). It is formed by interacting a functional peptide R4F having a α-helix structure with phospholipid and cholesteryl ester, and has a particle size of 30 nm or less. Such nanoparticle mainly targets to cells with high expression of scavenger receptor B (SR-B1) based on the function of the peptide. However, since SR-B1 is also highly expressed in the normal tissue cells (e.g. liver cells), the nanoparticle does not have a desired contrast in distribution between tumors and normal tissues, and may have potential toxic and side effects during transportation of chemotherapy drugs. In addition, the nanoparticle of WO2009073984 only functions as a tool for targeted delivery, and does not involve in the effects of tumor therapy.

In summary, it is necessary to develop a ultra-small particle-size (<40 nm) nanoparticle carrying a dual-targeted therapeutic peptide and simultaneously loading with an imaging contrast agent and a chemotherapy drug to be used for highly specific synchronous diagnosis and therapy of nasopharyngeal carcinoma, which will become a targeted nano-drug for nasopharyngeal carcinoma with great potential in clinical application.

MODE FOR INVENTION

To address the above problems, the present invention provides a targeted therapeutic peptide for nasopharyngeal carcinoma (LTVSPWYLTVSPWY, SEQ ID NO:3), and a dual-targeted therapeutic peptide for nasopharyngeal carcinoma (referred to as dtTP$_{NPC}$) capable of controlling the size of lipid nanoparticles, as well as a dual-targeted diagnostic and therapeutic nanoparticle for nasopharyngeal carcinoma (referred to as dtDTNP$_{NPC}$) carrying the dtTP$_{NPC}$ and uses thereof. The peptide and nanoparticle can efficiently and specifically target to nasopharyngeal carcinoma, and significantly inhibit the growth of nasopharyngeal tumor cells, and thus, can be used in the clinical treatment.

The present invention provides a technical solution of covalently linking a targeted therapeutic peptide for nasopharyngeal carcinoma with another targeted therapeutic peptide for nasopharyngeal carcinoma having an α-helical structure (the α-helical peptide is a targeted therapeutic peptide capable of forming an α-helical structure via interaction with a phospholipid) through a peptide linker in sequence. The resulted peptide can be used for dual-targeted therapy of nasopharyngeal carcinoma and size control of lipid nanoparticles.

An amino acid sequence of the dual-targeted therapeutic peptide for nasopharyngeal carcinoma is:

```
                                          (SEQ ID NO: 1)
       FAEKFKEAVKDYFAKFWDGSGLTVSPWYLTVSPWY.
```

Preferably, the amino acid sequence of the said targeted therapeutic peptide for nasopharyngeal carcinoma is:

```
                                          (SEQ ID NO: 3)
              LTVSPWYLTVSPWY.
```

The present invention also provides a dual-targeted diagnostic and therapeutic nanoparticle for nasopharyngeal carcinoma consisting of three components: 1) a dual-targeted therapeutic peptide for nasopharyngeal carcinoma capable of controlling size of lipid nanoparticles; 2) phospholipid and cholesteryl ester for composing the shell of the nanoparticle and maintaining a stable spherical nano-structure; 3) a cargo which is an imaging contrast agent, a drug or the combination thereof, wherein the imaging contrast agent may be a fluorescent dye modified with cholesteryl ester (DiR-BOA or Fluo-BOA), and the drug may be paclitaxel or curcumin.

The present invention has the following advantages.

1) Excellent physical and chemical properties: the nanoparticle has an average particle size of about 14.6 nm, measured by dynamic laser scattering, with uniform particle size and good dispersibility, and without aggregation.

2) Good biocompatibility: the raw materials used for preparing the nanoparticles are the phospholipid, the cholesteryl ester, and the dual-targeted therapeutic peptide for nasopharyngeal carcinoma, each of them has been used in clinical trials and has good biological compatibility.

3) Simple preparation process and easy to be scaled up.

4) Good targeting effect: at the cellular level, the present dtDTNP$_{NPC}$ shows a stronger targeting ability compared to the nanoparticle formed from α-helical peptide (referred to as NP), and it is easier to be taken up by nasopharyngeal carcinoma cells (e.g. 5-8 F cells, SUNE-1 cells and the like) compared with the other tumor cells such as liver tumor cells, Hela cells and the like; and at the in vivo level, the present dtDTNP$_{NPC}$ can selectively target to and accumulate in tumor sites, 12 h after tail vein injection to the nude mice bearing the nasopharyngeal carcinoma 5-8 F tumor.

5) Good curative effect: at the cellular level, the present nanoparticle can significantly induce cell death 1 h after incubated with nasopharyngeal carcinoma 5-8 F cells; and it showed in living animal experiments that the present nanoparticle has greatly improved abilities to be accumulated in nasopharyngeal carcinoma tissue and to be taken up by nasopharyngeal carcinoma cells due to the dual-targeted effect and EPR effect (enhanced permeability and retention effect) on solid tumor, and thus has improved good inhibitory activity against growth of tumor cells.

6) Low toxic and side effect: Starting from the third day after being subcutaneously inoculated with nasopharyngeal carcinoma 5-8 F cells, nude mice were injected with the present dtDTNP$_{NPC}$ into the tail vein every other day until the 14th day. The animal experiments demonstrated that no significant changes in body weight had been found in the nude mice, compared with the control group treated with PBS.

7) Extendable Function: the present nanoparticle not only can vary the targeted peptide for targeted therapy of different tumors, but also can be loaded with a dye (DiR-BOA) and/or a lipid-soluble drug (for example paclitaxel and curcumin, etc.) for diagnosis and therapy of diseases in its core to achieve a perfect combination of dual-targeted therapy and immunotherapy for tumor.

BRIEF DESCRIPTION OF ACCOMPANYING DRAWINGS

Hereinafter, the present invention will be described in more detail in connection with the accompanying drawings and embodiments.

Figure 29:
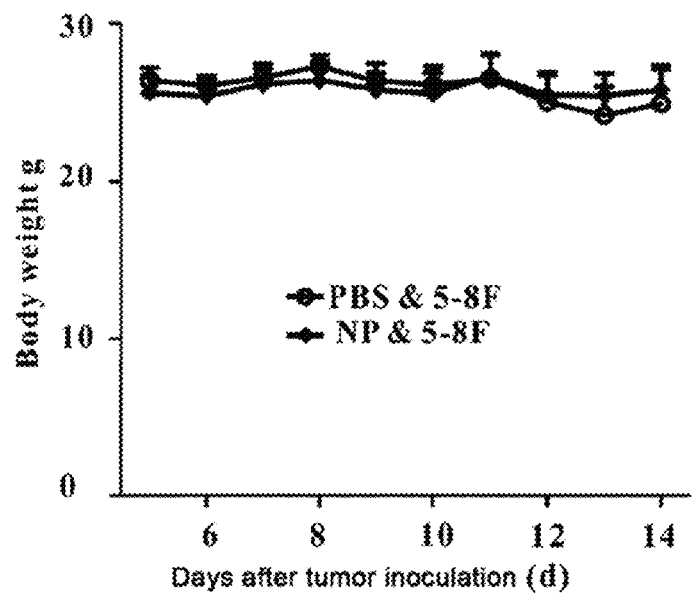
Figure 30:
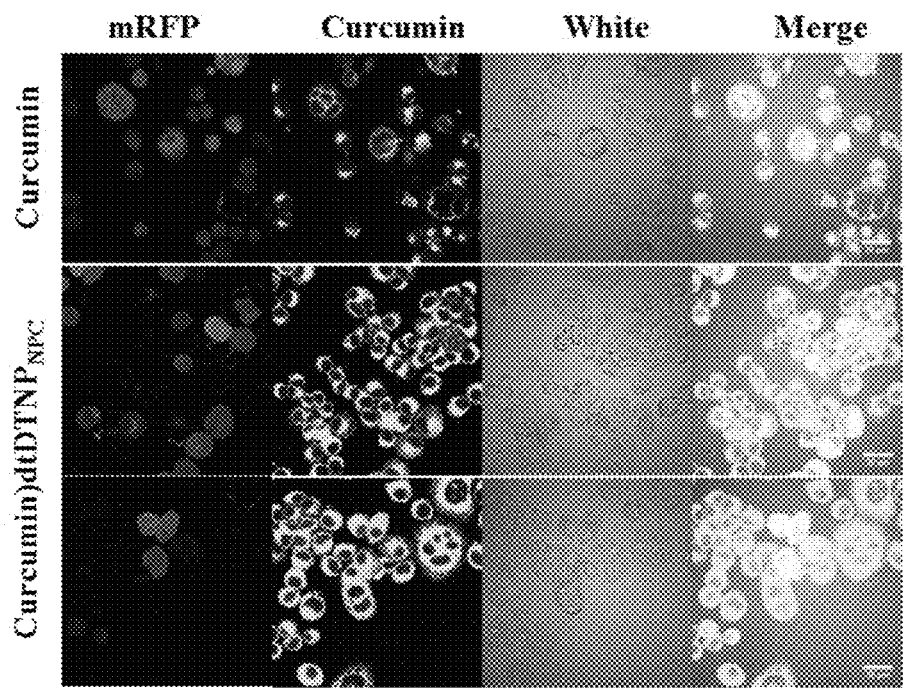

FIG. 29 is a curve showing the changes in body weight of tumor-bearing nude mice in the experimental group and the control group by tail vein injection of 2.5 nmol NP or PBS to the nude mice every other day until the 14th day, starting from the third day after the nude mice was subcutaneously inoculated with 5-8 F, in Example 5; and FIG. 30 shows the results of laser confocal imaging of cells, after incubating nasopharyngeal carcinoma 5-8 F cells with dtDTNP$_{NPC}$ loaded with curcumin and free curcumin for 1 h in Example 7.

BEST MODE FOR CARRYING OUT THE INVENTION

Example 1

Figure 1:
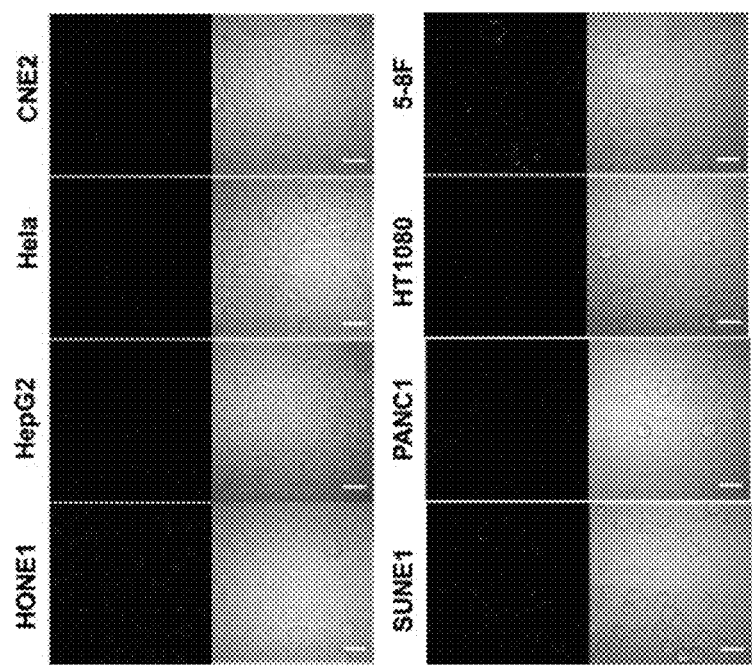
FIG. 1 shows the results of laser confocal imaging with Octa-FNP fluorescent nano-probes for different tumor cells incubated for 3 h in Example 1.
Figure 2:
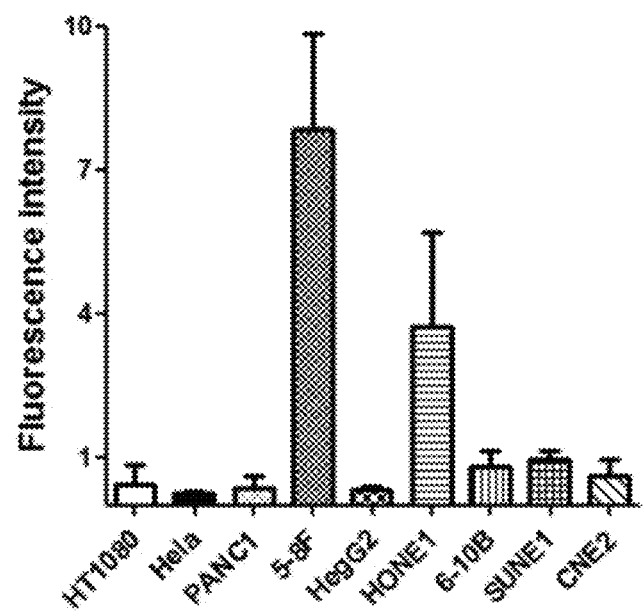
FIG. 2 shows the quantitative results of FACS flow cytometry with Octa-FNP fluorescent nano-probes for different tumor cells incubated for 3 h in Example 1.

In this example, a peptide octavalent fluorescent nanoprobe based on tetramer far-red fluorescent protein was prepared by using a method for constructing a peptide fluorescent probe having a multivalent effect and a nanosized effect invented in the previous research. The probe was used to detect and screen different types of tumor cell lines, in order to screen and identify the tumor-targeting property of the peptide, LTVSPWYLTVSPWY (SEQ ID NO: 3). As shown from the results in FIG. 1, the peptide LTVSPWYLTVSPWY (SEQ ID NO: 3) not only has an excellent tumor-targeting property to nasopharyngeal carcinoma cells, but also can effectively induce the death of tumor cells. FIG. 2 shows the quantitative results of FACS flow cytometry after incubating different tumor cells with the Octa-FNP fluorescent nanoprobe for 3 h. It can be seen that the octavalent fluorescent nanoprobe based on the peptide LTVSPWYLTVSPWY (SEQ ID NO: 3) is more likely to be absorbed by nasopharyngeal carcinoma cells (such as 5-8 F cells, SUNE-1 cells, HONE-1 cells and so on), compared with other cancer (such as liver cancer and cervical cancer) cells.

Example 2

In this example, two specifically targeted therapeutic peptides for nasopharyngeal carcinoma, LTVSPWYLTVSPWY (SEQ ID NO: 3) and FAEKFKEAVKDYFAKFWD (SEQ ID NO: 2), were linked via a sequence of GSG to form a new dual-targeted therapeutic peptide for nasopharyngeal carcinoma (referred to as dtTP$_{NPC}$). The complete amino acid sequence thereof is described as SEQ ID NO: 1 in the sequence listing.

Dual-targeted diagnostic and therapeutic nanoparticles for nasopharyngeal carcinoma (referred to as dtDTNP$_{NPC}$) were prepared by using the dtTP$_{NPC}$ through the following steps:

1) 3 µmol of DMPC (1,2-dimyristoyl-sn-glycero-3-phosphocholine) and 0.225 µmol of DiR-BOA (or 0.1 µmol cholesteryl oleate, referred to as C.O) in chloroform were fully mixed in a glass test tube, and the tube was sealed with parafilm;

2) the chloroform in the tube was blown off under a stable nitrogen flow so that the mixture in step 1) formed a thin film at the bottom of the tube;

3) the tube was put into a vacuum desiccator and dried in vacuum for 1 h;

4) the tube was added with 1 ml of phosphate buffer, and slightly oscillated by using a vortex shaker;

5) the tube was sonicated in a water bath at 48° C. for 30-60 min until the solution became clear;

6) a PBS solution containing 0.36 µmol of $dtTP_{NPC}$ was injected into the sealed tube using a syringe, and the tube was fully mixed and sealed, and left overnight at 4° C.

7) on the next day, the mixture was purified by using a FPLC system, the $dtTPNP_{NPC}$-rich solution was collected and concentrated to be ready for use.

Figure 3:
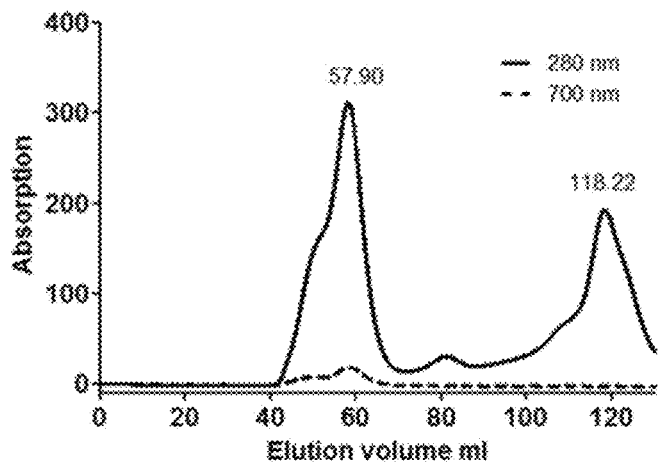
FIG. 3 is a dual band absorbance-elution volume curve of two synthetic units of dtDTNP$_{NPC}$ loaded with 0.4 μmol of DiR-BOA, a fluorescent dye, in the core [described as: 0.4 μmol (DiR-BOA) dtDTNP$_{NPC}$] purified by FPLC system in Example 2.
Figure 4:
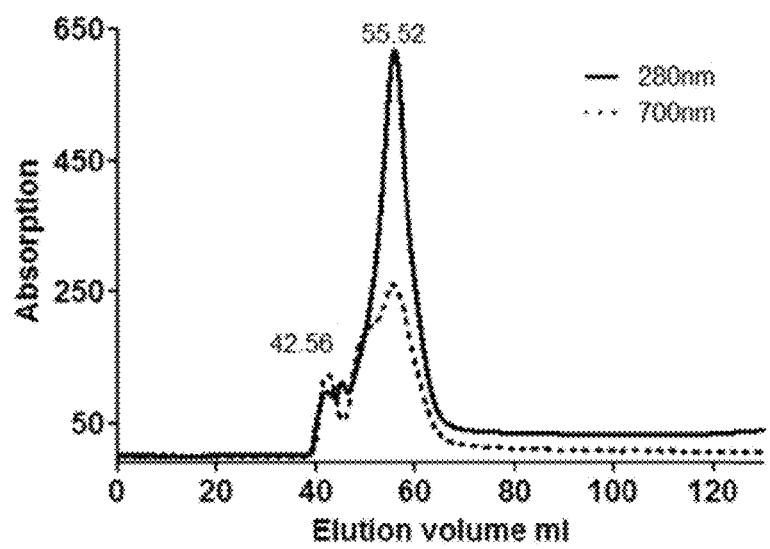
FIG. 4 is a dual band absorbance-elution volume curve of two synthetic units of 0.45 μmol (DiR-BOA) dtDTNP$_{NPC}$ purified by FPLC system in Example 2.
Figure 5:
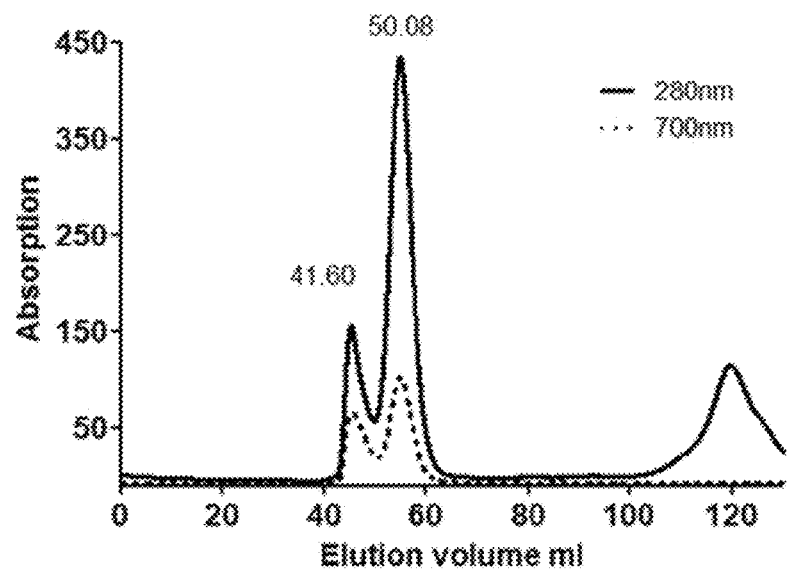
FIG. 5 is a dual band absorbance-elution volume curve of two synthetic units of 0.5 μmol (DiR-BOA) dtDTNP$_{NPC}$ purified by FPLC system in Example 2.

In order to study the specific tumor-targeting ability of the $dtDTNP_{NPC}$, a fluorescent dye, DiR-BOA (a near infrared fluorescent dye modified with cholesteryl ester, and having excitation and emission wavelengths of 748 nm and 780 nm, respectively), was loaded in core so that the nanoparticles are capable of dual-targeted diagnosis and therapy of nasopharyngeal carcinoma. A $dtDTNP_{NPC}$ having a suitable particle size and a certain loading was obtained by adjusting the ratio of the fluorescent dye DiR-BOA to the peptide and the phospholipid. FPLC Purification results are shown in FIGS. 3 to 4. FIG. 3 is a dual band absorbance-elution volume curve of two synthetic units of 0.4 µmol (DiR-BOA)$dtDTNP_{NPC}$ purified by FPLC system. At this synthetic ratio, there are a lot of free peptides at around 118 min, and the peak absorbance value of DiR-BOA is very low, showing that the loading efficiency for DiR-BOA is very low. When DiR-BOA core-loaded into 2 synthetic units of nanoparticles was adjusted to 0.45 µmol, the obtained results are shown in FIG. 4. At this synthetic ratio, a peak appears at 55.52 min for most of the obtained nanoparticles. Although there is a tiny peak at 42.56 min, its proportion is much small compared to the integral area of the optimal peak of the nanoparticles, and there is hardly any free peptide. When DiR-BOA core-loaded into 2 synthetic units of nanoparticles was adjusted to 0.5 µmol, as shown in FIG. 5, the optimal appearance time for the nanoparticles is advanced to 50.08 min from the original 55.52 min, and the tiny peak at 42.56 min is changed to a large peak at 41.60 min, and a lot of free peptides appeared at 118 min. Therefore, the efficiency for synthesizing the nanoparticles at this ratio is greatly reduced. Thus, to synthesize (DiR-BOA)$dtDTNP_{NPC}$ with an appropriate particle size, the optimal ratio for each component is 6 µmol of DMPC, 0.45 µmol of DiR-BOA, and 0.72 µmol of $dtTP_{NPC}$.

Figure 6:
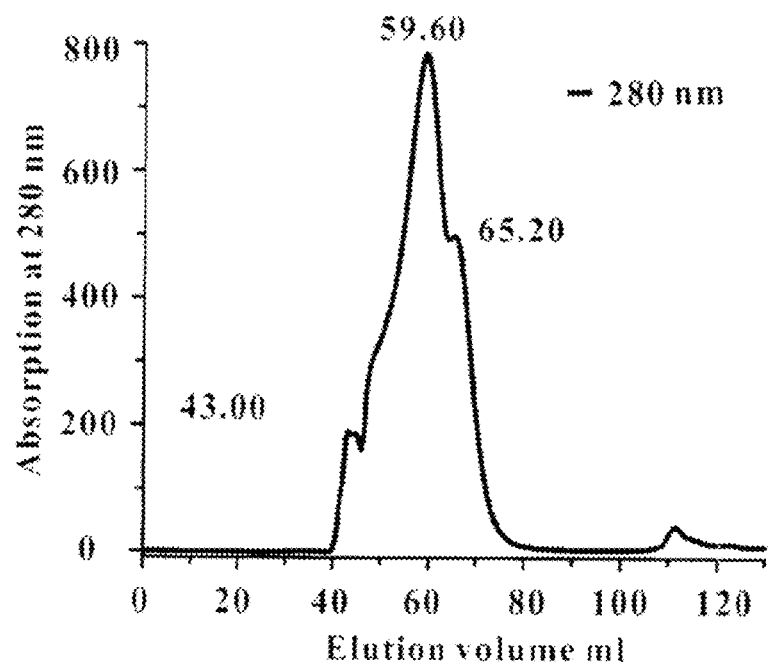
FIG. 6 is a dual band absorbance-elution volume curve of one synthetic unit of dtDTNP$_{NPC}$ loaded with 0.1 μmol cholesteryl ester in the core, purified by FPLC system in Example 2.

In order to study on the dual-targeted therapeutic property of the peptide for nasopharyngeal carcinoma, the near infrared fluorescent dye, DiR-BOA, was replaced with cholesteryl ester to obtain nanoparticles having a suitable particle size. Results of FPLC Purification are shown in FIG. 6. The appearance time for the nanoparticles is at 59.60 min, and only a few free peptides appears at 118 min, indicating that the above optimized ratio is suitable for cholesteryl ester. The ratio of the raw materials is 3 µmol of DMPC, 0.1 µmol of C.O, and 0.36 µmol of $dtTP_{NPC}$.

Figure 7:
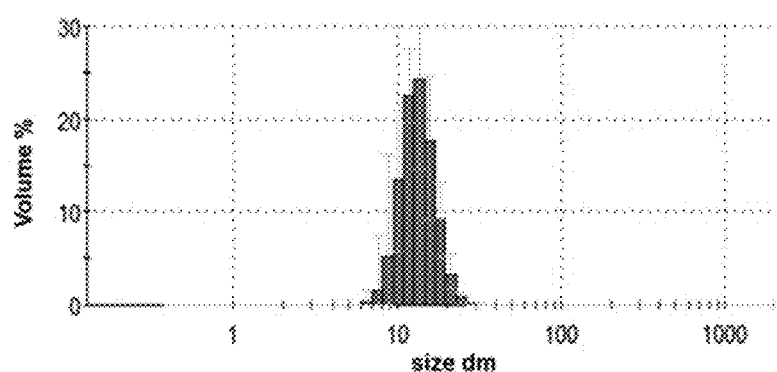
FIG. 7 is a graph showing the particle size distribution of dtDTNP$_{NPC}$ measured on dynamic laser scattering (DLS) system in Example 2.
Figure 8:
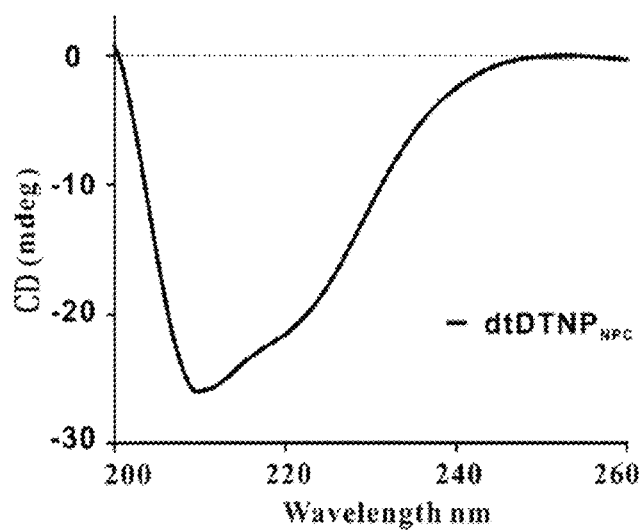
FIG. 8 is a spectrum on the α-helical structure of the peptide in the dtDTNP$_{NPC}$ measured on a circular dichroism spectrometer in Example 2.
Figure 9:
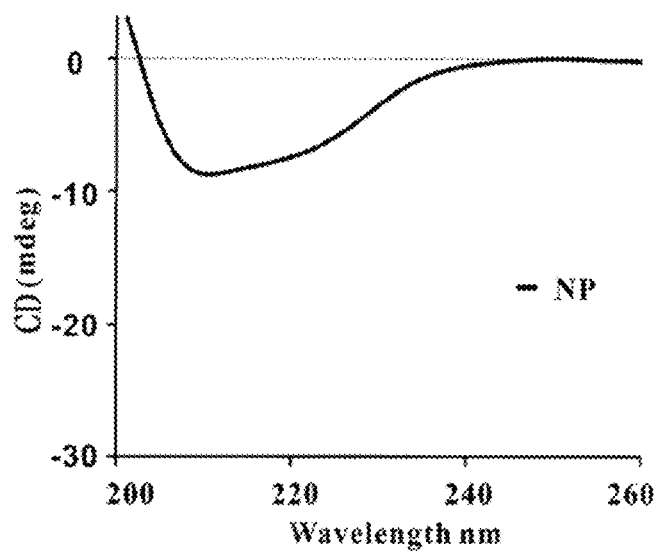
FIG. 9 is a spectrum on the α-helix structure of the peptide in the NP measured on a circular dichroism spectrometer in Example 2.

The particle size of the purified $dtDTNP_{NPC}$ was measured on a dynamic laser scattering (DLS) system and the results are shown in FIG. 7. The average particle size is 14.60±1.64 nm, and the nanoparticles have a uniform size and a good monodispersity. FIG. 8 shows the measurement on the α-helical structure of the peptide in $dtDTNP_{NPC}$ by using a circular dichroism spectrometer, and it shows that, the synthesized $dtDTNP_{NPC}$ has a stronger α-helical structure, compared with the circular dichroism results of NP in FIG. 9.

Example 3

Figure 10:
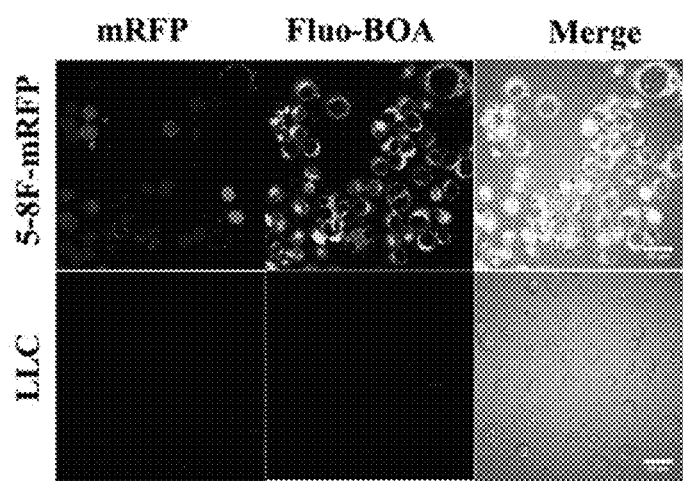
FIG. 10 shows the laser confocal imaging results after incubating 5-8 F-mRFP cells and lung cancer cells (LLC) with (Fluo-BOA)dtDTNP$_{NPC}$ respectively for 1 h in Example 3.
Figure 11:
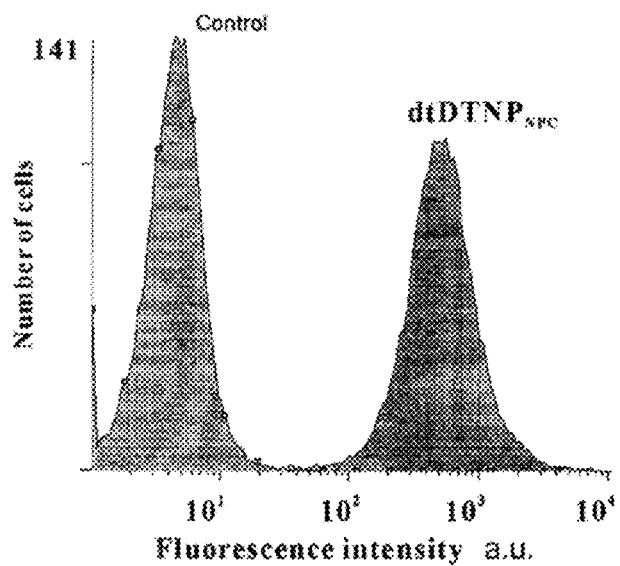
FIG. 11 is a histogram measured on a flow cytometer after incubating nasopharyngeal carcinoma 5-8 F cells with (DiR-BOA)dtDTNP$_{NPC}$ for 1 h in Example 3.
Figure 12:
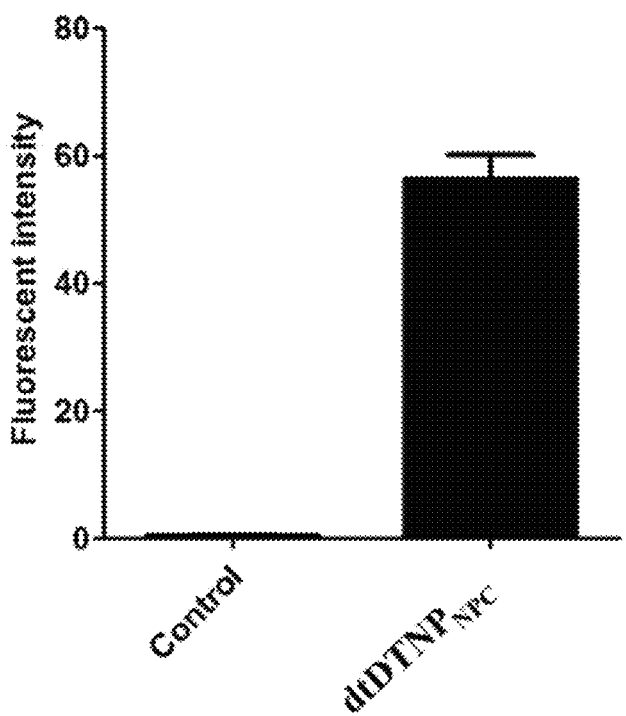
FIG. 12 shows the fluorescence quantitative results measured on a flow cytometer after incubating nasopharyngeal carcinoma 5-8 F cells with (DiR-BOA)dtDTNP$_{NPC}$ for 1 h in Example 3.
Figure 13:
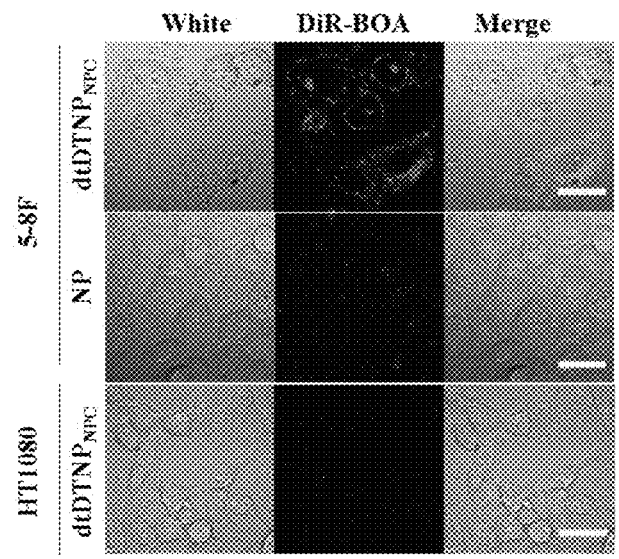
FIG. 13 shows the laser confocal imaging results after respectively incubating 5-8 F cells and human fibrosarcoma HT1080 cells with (DiR-BOA)dtDTNP$_{NPC}$ and (DiR-BOA) NP for 1 h in Example 3.
Figure 14:
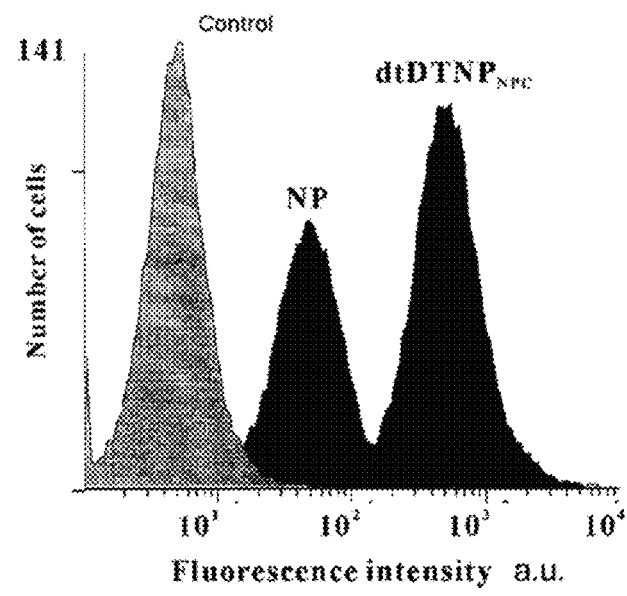
FIG. 14 is a histogram measured on a flow cytometer after incubating nasopharyngeal carcinoma 5-8 F cells with (DiR-BOA)dtDTNP$_{NPC}$ and (DiR-BOA) NP for 1 h in Example 3.
Figure 15:
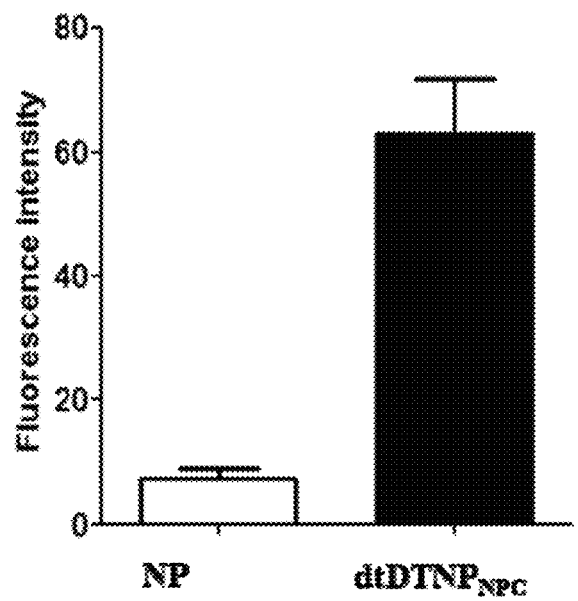
FIG. 15 shows fluorescence quantitative results measured on a flow cytometer after incubating nasopharyngeal carcinoma 5-8 F cells with (DiR-BOA)dtDTNP$_{NPC}$ and (DiR-BOA) NP for 1 h in Example 3.
Figure 16:
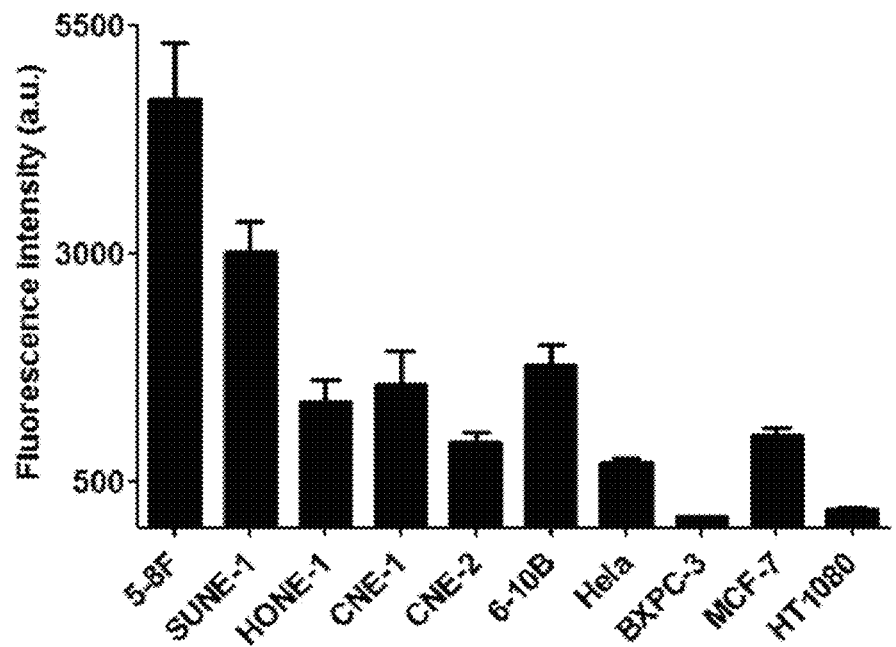
FIG. 16 shows fluorescence quantitative results on cell uptake after incubating nasopharyngeal carcinoma 5-8 F, HONE-1, 6-10B, CNE2, SUNE-1 and CNE-1 cells and tumor HT1080, Hela, BXPC-3 and MCF-7 cells (DiR-BOA) with dtDTNP$_{NPC}$ at 37° C. for 3 h in Example 3.

FIG. 10 shows the experimental results of the tumor cell-targeting properties of the Fluo-BOA or DiR-BOA core-loaded $dtDTNP_{NPC}$s prepared in Example 2. Laser confocal imaging was performed after incubating nasopharyngeal carcinoma 5-8 F cells and lung cancer LLC cells respectively with 2 µmol (Fluo-BOA)$dtDTNP_{NPC}$ for 1 h, and the results show that the $dtDTNP_{NPC}$ are easier to be taken up by nasopharyngeal carcinoma 5-8 F cells. Also, laser confocal imaging was carried out after incubating nasopharyngeal carcinoma 5-8 F cells and human fibrosarcoma HT1080 cells with 2 µmol (DiR-BOA)$dtDTNP_{NPC}$ and (DiR-BOA)NP for 1 h respectively. The flow cytometry results show that the 5-8 F cells treated with (DiR-BOA)$dtDTNP_{NPC}$ have a significantly improved fluorescence intensity, compared with the blank control (as shown in FIGS. 11-12). As for the comparison of the targeting ability to tumor cells between the (DiR-BOA)$dtDTNP_{NPC}$ and the NP, the imaging results in FIG. 13 show that $dtDTNP_{NPC}$ can be selectively taken up by 5-8 F cells, indicating that they are capable of selectively targeting to the nasopharyngeal carcinoma cells. For quantitatively determining the ability of nasopharyngeal carcinoma cells to take up the (DiR-BOA)$dtDTNP_{NPC}$, a flow cytometry measurement was carried out after incubating nasopharyngeal carcinoma 5-8 F cells with (DiR-BOA)$dtDTNP_{NPC}$ containing 8 µmol peptides and (DiR-BOA)NP containing 8 µmol peptides for 1 h. As shown in FIG. 14 and FIG. 15, compared with those incubated with (DiR-BOA)NP, the nasopharyngeal carcinoma 5-8 F cells incubated with (DiR-BOA)$dtDTNP_{NPC}$ have a significantly improved fluorescence intensity, which is about 9 times of that of (DiR-BOA)NP. In order to study the selectively targeting property of the $dtDTNP_{NPC}$, nasopharyngeal carcinoma 5-8 F, HONE-1, 6-10B, CNE2, SUNE-1 and CNE-1 cells and tumor HT1080, Hela, BXPC-3 and MCF-7 cells were incubated with (DiR-BOA)$dtDTNP_{NPC}$ at 37° C. for 3 h. As shown in FIG. 16, (DiR-BOA)$dtDTNP_{NPC}$ can selectively target to nasopharyngeal carcinoma 5-8 F cells and SUNE-1 cells.

Figure 17:
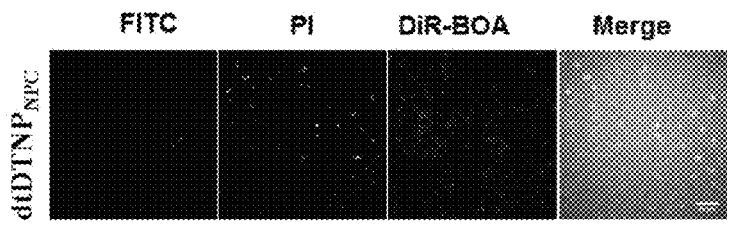
FIG. 17 shows laser confocal imaging results of identification of cell death manner through Annexin V-FITC/PI apoptosis agent after incubating nasopharyngeal carcinoma 5-8 F cells with (DiR-BOA)dtDTNP$_{NPC}$ for 1 h in Example 3.
Figure 18:
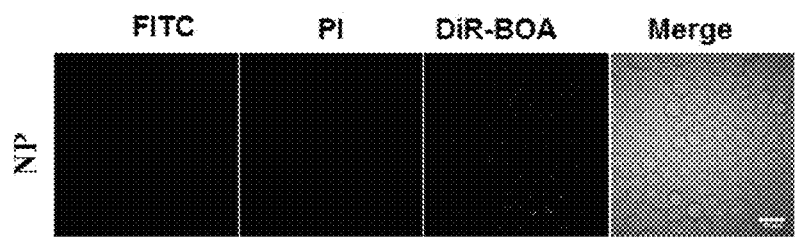
FIG. 18 shows the results of the laser confocal imaging by identification of cell death manner through Annexin V-FITC/PI apoptosis agent after incubating nasopharyngeal carcinoma 5-8 F cells with (DiR-BOA)NP for 1 h in Example 3.
Figure 19:
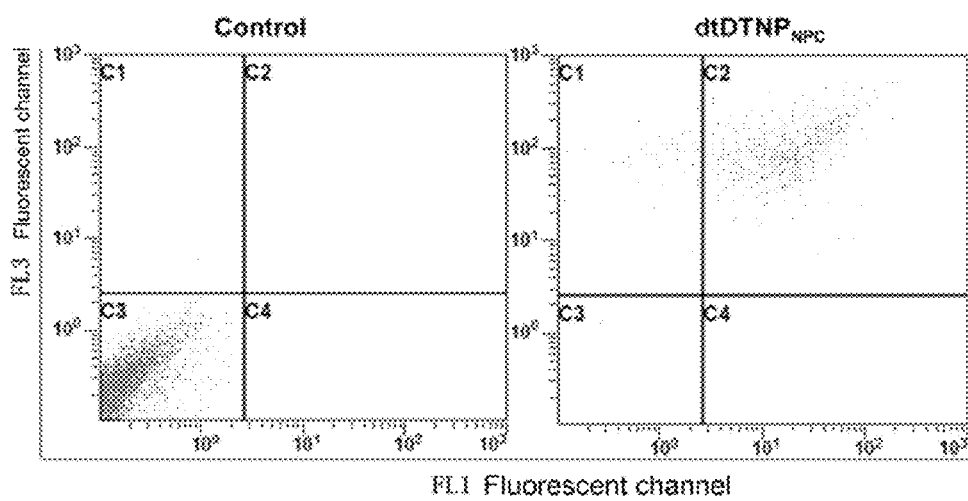
FIG. 19 shows the results of measurement on the number of death cells and identification of cell death manner on a flow cytometer and by Annexin V-FITC/PI apoptosis agent, after incubating nasopharyngeal carcinoma 5-8 F cells with (DiR-BOA)dtDTNP$_{NPC}$ for 1 h in Example 3.
Figure 20:
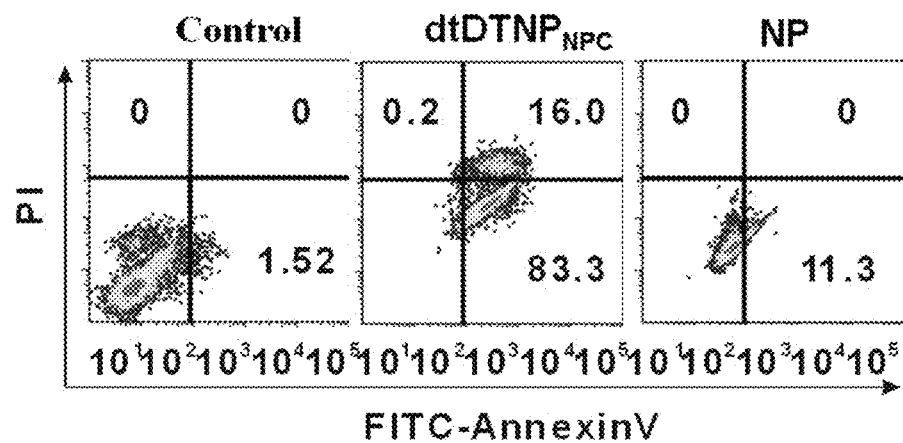
FIG. 20 shows the quantitative measurement results on the ratio and manner of cell death by Annexin V-FITC/PI apoptosis agent, after incubating nasopharyngeal carcinoma 5-8 F cells with (DiR-BOA)dtDTNP$_{NPC}$ and (DiR-BOA)NP for 1 h in Example 3.

In order to study whether the $dtDTNP_{NPC}$ induce apoptosis or necrosis of nasopharyngeal carcinoma 5-8 F cells, a quantitative determination on FITC/PI fluorescent signal of cells by using Annexin V-FITC/PI agent was performed after incubating nasopharyngeal carcinoma 5-8 F cells with 2 µmol (DiR-BOA)$dtDTNP_{NPC}$ and (DiR-BOA)NP for 1 h. FIGS. 17-18 show the results of detecting the three fluorescent signals of DiR-BOA, FITC and PI through laser confocal imaging. Compared with the (DiR-BOA)NP control group, (DiR-BOA)$dtDTNP_{NPC}$ treatment group showed a very strong fluorescent signal in DiR channel, and at the same time, some cells showed a strong PI signal in PI channel, indicating the death of some cells, while the fluorescent signal in FITC channel is weak. Therefore, a preliminary judgment was that the (DiR-BOA)$dtDTNP_{NPC}$ induce necrosis of the nasopharyngeal carcinoma 5-8 F cells. A quantitative determination was further carried out on the fluorescent signal intensity of cells treated with (DiR-BOA)$dtDTNP_{NPC}$ in FITC and PI channels on a flow cytometer. The results in FIG. 19 show that (DiR-BOA)$dtDTNP_{NPC}$ can induce apoptosis of nasopharyngeal carcinoma 5-8 F cells. In order to quantitatively investigate the effects of $dtDTNP_{NPC}$ on inducing apoptosis of 5-8 F cells, nasopharyngeal carcinoma 5-8 F cells were incubated respectively with (DiR-BOA)dtDTNP$_{NPC}$ containing 8 µmol peptides and (DiR-BOA)NP containing 8 µmol peptides for 1 h, and then counterstained by a Annexin V-FITC/PI agent, and finally a measurement on the fluorescent signal intensity in FITC (FL1)/PI (FL3) channels was performed on a flow cytometer to determine the cell number of apoptosis or necrosis. The results in FIG. 20 show that, compared with those of the (DiR-BOA)NP control group, the tumor cells incubated with (DiR-BOA)dtDTNP$_{NPC}$ have strong signals in both FL1 and FL3 channels, indicating that the (DiR-BOA)dtDT-NP$_{NPC}$ mainly kill nasopharyngeal carcinoma 5-8 F cells via necrosis mechanism.

Example 4

In vivo targeting property of the (DiR-BOA)dtDTNP$_{NPC}$ prepared in Example 2 was evaluated.

Figure 21:
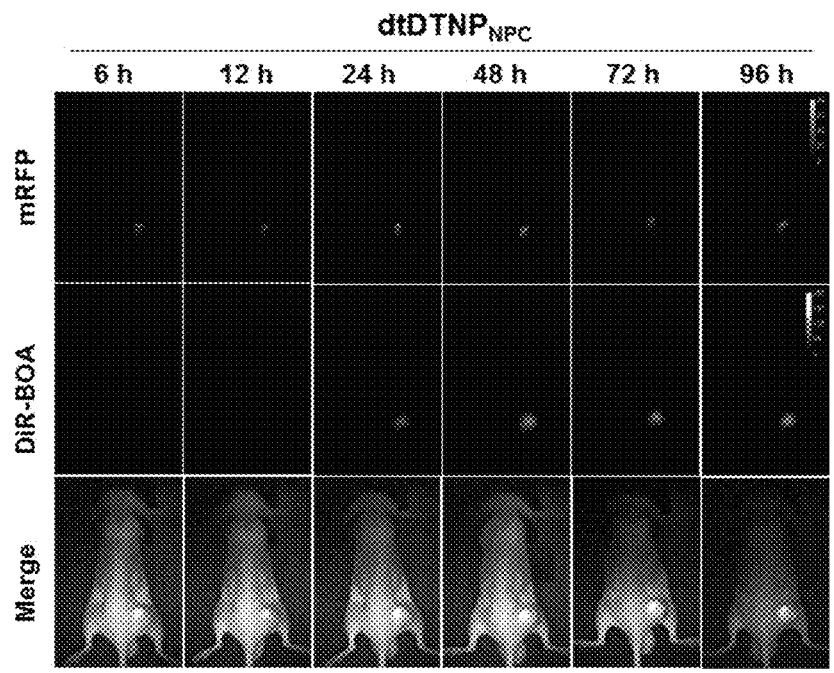
FIG. 21 shows the results of whole-body fluorescence imaging at 3 h, 6 h, 12 h, 24 h, 48 h, 72 h and 96 h after tail vein injection of 2.5 nmol (DiR-BOA)dtDTNP$_{NPC}$ in Example 4.
Figure 22:
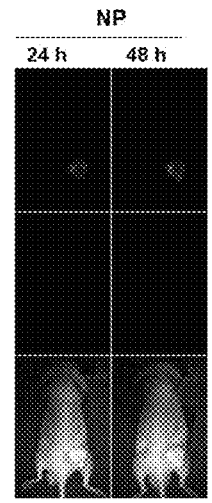
FIG. 22 shows the results of whole-body fluorescence imaging at 24 h and 48 h after tail vein injection of 2.5 nmol (DiR-BOA)NP in Example 4.
Figure 23:
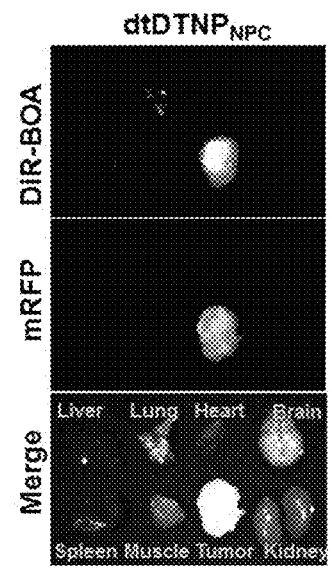
FIG. 23 shows the results of whole-body fluorescence imaging of various organs at 48 h after tail vein injection of 2.5 nmol (DiR-BOA)dtDTNP$_{NPC}$ in Example 4.
Figure 24:
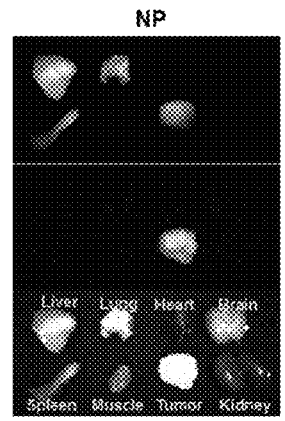
FIG. 24 shows the results of whole-body fluorescence imaging of various organs at 48 h after tail vein injection of 2.5 nmol (DiR-BOA)NP in Example 4.
Figure 25:
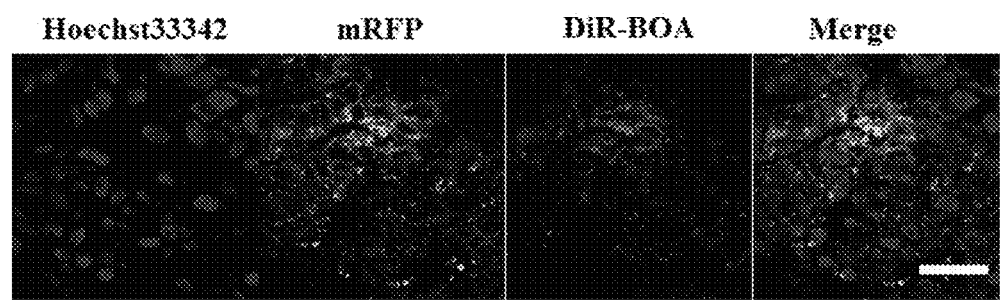
FIG. 25 shows the results of fluorescence imaging of a frozen section of tumor tissue at 48 h after tail vein injection of 2.5 nmol (DiR-BOA)dtDTNP$_{NPC}$ in Example 4.
Figure 26:
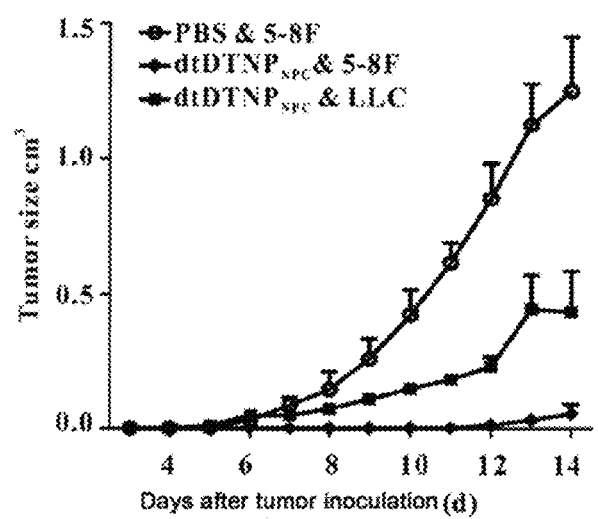
FIG. 26 is a curve showing the changes in tumor volume by tail vein injection of 2.5 nmol dtDTNP$_{NPC}$ or PBS to nude mice every other day until the 14th day, starting from the third day after the nude mice was subcutaneously inoculated with 5-8 F or LLC tumor cells, in Example 5.

$1 \times 10^6$ 5-8 F cells were subcutaneously inoculated into nude mice to construct nasopharyngeal carcinoma tumor-bearing nude mice model. A whole-body fluorescence imaging was carried out on the tumor-bearing nude mice, when the 5-8 F tumor volume reached to 0.5 cm$^3$. Four time points were set for exposure in general. 2.5 nmol (DiR-BOA)dtDTNP$_{NPC}$ and (DiR-BOA)NP were then injected into tail vain. The whole-body fluorescence imaging was carried out at 3 h, 6 h, 12 h, 24 h, 48 h, 72 h and 96 h after the tail-vein injection, and the selected exposure time was the same as that before the tail-vein injection. A xenon light source, an excitation filter of 716/40 nm, and a 800FS40-25 band pass filter as the receiving filter were used in the whole-body fluorescence imaging system. In order to obtain a better signal-to-noise ratio, an excitation filter of 685/40 nm was used to collect the autofluorescence from tissues, and the autofluorescence was deducted in the subsequent image processing to eliminate its interference to fluorescent signals. As shown in FIG. 21, the (DiR-BOA) dtDTNP$_{NPC}$ could effectively accumulate in 5-8 F tumor at 24 h after the tail vein injection, and 5-8 F tumor showed the strongest fluorescent signal at 48 h, and the best signal-to-noise ratio between 5-8 F tumor and normal tissue appeared after 72 h. However, for the (DiR-BOA)NP group, no fluorescent signal was detected in the tumor site at 24 h and 48 h after the tail vein injection, as shown in FIG. 22. The in vivo dynamic fluorescence imaging fully confirmed that the dtDT-NP$_{NPC}$ are capable of targeting to the tumor. At 48 h after the tail vein injection, each of the organs was excised to perform the whole-body fluorescence imaging. The results further showed that, the targeted accumulation mainly occurred at the tumor site in the (DiR-BOA)dtDTNP$_{NPC}$ group (as shown in FIG. 23), while (DiR-BOA)NP had strong accumulation in liver, spleen and lung besides partial accumulation in the tumor site (as shown in FIG. 24). In order to study the penetrability of (DiR-BOA) dtDTNP$_{NPC}$, frozen section were carried out on the tumor treated with (DiR-BOA)dtDTNP-$_{NPC}$. As shown in FIG. 25, the tumor site had a very strong DiR-BOA fluorescent signal, indicating that dtDTNP$_{NPC}$ have very strong penetrability to solid tumor of nasopharyngeal carcinoma.

Example 5

In vivo therapeutic efficacy of dtDTNP$_{NPC}$ prepared in Example 2 against nasopharyngeal carcinoma tumor was evaluated.

Nude mice models with subcutaneous nasopharyngeal carcinoma 5-8 F and lung cancer LLC were constructed. LLC tumor was used as the negative control group for the targeting property of dtDTNP$_{NPC}$. 5-8 F and LLC cells were digested, rinsed twice with sterilized PBS, and then counted. The nude mice were inoculated with 5-8 F cells at $1 \times 10^6$ cells/animal. The inoculated tumor-bearing nude mice were randomly divided into PBS control group and 5-8 F tumor groups treated with dtDTNP$_{NPC}$ and NP. The nude mice in LLC tumor control group were subcutaneously inoculated with LLC cell at $2 \times 10^6$ cells/animal. The number of tumor-bearing nude mice in these three groups was 5 for each group. Tail vein injection of dtDTNP$_{NPC}$ started from the third day after the subcutaneous inoculation of tumor cells once every other day to perform therapy.

For PBS group, an isovolumic sterile PBS was tail-vein injected at 0.25 ml/animal.

For the 5-8 F tumor treatment groups, the dosage for the tail-vein injection was dtDTNP$_{NPC}$ and NP containing 10 nmol peptides.

For the LLC tumor treatment control group, the dosage for the tail-vein injection was dtDTNP$_{NPC}$ containing 10 nmol peptides.

The tumor volume of the nude mice inoculated subcutaneously with tumor cells was zero at day 3 and day 4, and the tumor began to appear at day 5. The tumor volume is calculated by the Formula: $V=0.5 \times L \times H \times H$.

Figure 27:
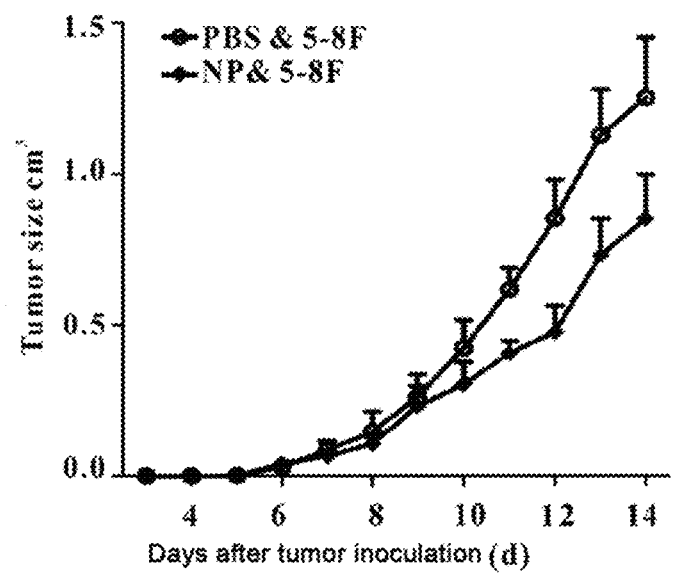
FIG. 27 is a curve showing the changes in tumor volume by tail vein injection of 2.5 nmol NP or PBS to nude mice every other day until the 14th day, starting from the third day after the nude mice was subcutaneously inoculated with 5-8 F, in Example 5.
Figure 28:
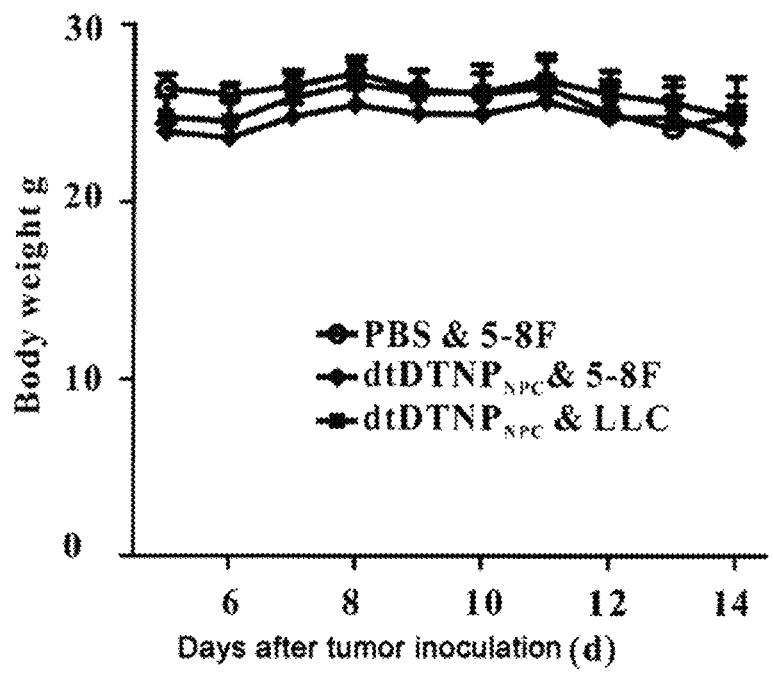
FIG. 28 is a curve showing the changes in body weight of tumor-bearing nude mice in the experimental group and the control group by tail vein injection of 2.5 nmol dtDTNP$_{NPC}$ or PBS to the nude mice every other day until the 14th day, starting from the third day after the nude mice was subcutaneously inoculated with 5-8 F or LLC tumor cells, in Example 5.

As shown in FIG. 26, 5-8 F tumor treatment groups showed a significantly inhibited tumor growth compared with the PBS control group, after 3 rounds of dtDTNP$_{NPC}$ administration. After 5 rounds of dtDTNP$_{NPC}$ administration, the growth of 5-8 F tumor was still be inhibited, while the LLC tumor volume was significantly increased, indicating that dtDTNP$_{NPC}$ have selectively inhibitory effect on nasopharyngeal carcinoma 5-8 F tumor. However, no significant difference in tumor was found between the NP treatment group and the PBS control group (as shown in FIG. 27). In terms of change in the body weight of the tumor-bearing nude mice, as shown in FIGS. 28 and 29, no significant difference was found between the tumor-bearing mice of dtDTNP$_{NPC}$ and NP treatment groups and the PBS control group after 6 rounds of treatment, indicating that the dtDTNP$_{NPC}$ at the treatment concentration have no obvious toxic and side effect on the tumor-bearing nude mice.

Example 6

The cholesteryl oleate used for preparing dtDTNP$_{NPC}$ in Example 2 was partially replaced with paclitaxel (PTX-OL), a fat-soluble drug. (PTX-OL)dtDTNP$_{NPC}$ nanoparticles were formed by using phospholipid, dtTP$_{NPC}$ and paclitaxel, and can achieve the effect of dual-targeted combined therapy for nasopharyngeal carcinoma.

Example 7

The cholesteryl oleate used for preparing dtDTNP$_{NPC}$ in Example 2 was partially replaced with curcumin, a fat-soluble drug. (Curcumin)dtDTNP$_{NPC}$ were formed by using phospholipid, dtTP$_{NPC}$ and curcumin, and showed good killing effect on nasopharyngeal carcinoma cells. As shown in FIG. 30, confocal fluorescence imaging was carried out after incubating 5-8 F-mRFP cells with free curcumin and dtDT-NP$_{NPC}$ containing 2 µmol of curcumin for 1 h respectively, and (Curcumin)dtDTNP$_{NPC}$ are more likely to be taken up by 5-8 F-mRFP and have a better killing effect, compared with free curcumin.

What is claimed:

1. A peptide for nasopharyngeal carcinoma, wherein the peptide for nasopharyngeal carcinoma is formed by covalently linking FAEKFKEAVKDYFAKFWD (SEQ ID NO:2), a peptide linker and LTVSPWYLTVSPWY (SEQ ID NO:3) in sequence.

2. The peptide for nasopharyngeal carcinoma according to claim 1, wherein the amino acid sequence of the peptide for nasopharyngeal carcinoma is:

(SEQ ID NO: 1)
FAEKFKEAVKDYFAKFWDGSGLTVSPWYLTVSPWY.

3. A nanoparticle for nasopharyngeal carcinoma consisting of:
- a peptide for nasopharyngeal carcinoma formed by covalently linking FAEKFKEAVKDYFAKFWD (SEQ ID NO:2), a peptide linker and LTVSPWYLTVSPWY (SEQ ID NO:3) in sequence;
- a phospholipid;
- a cholesteryl ester; and
- a cargo.

4. The nanoparticle for nasopharyngeal carcinoma according to claim 3, wherein the cargo is an imaging contrast agent, a drug, or combinations thereof.

5. The nanoparticle for nasopharyngeal carcinoma according to claim 4, wherein the imaging contrast agent is a fluorescent dye modified with cholesteryl ester.

6. The nanoparticle for nasopharyngeal carcinoma according to claim 5, wherein the fluorescent dye is DiR-BOA or Fluo-BOA.

7. The nanoparticle for nasopharyngeal carcinoma according to claim 4, wherein the drug is paclitaxel or curcumin.

8. The nanoparticle for nasopharyngeal carcinoma according to claim 3, wherein the phospholipid is DMPC (1,2-dimyristoyl-sn-glycero-3-phosphocholine).

9. A method for diagnosis or treatment of nasopharyngeal carcinoma, comprising,
- administering to a subject in need thereof a nanoparticle for nasopharyngeal carcinoma consisting of:
- a peptide for nasopharyngeal carcinoma formed by covalently linking FAEKFKEAVKDYFAKFWD (SEQ ID NO:2), a peptide linker and LTVSPWYLTVSPWY (SEQ ID NO:3) in sequence;
- a phospholipid:
- a cholesteryl ester; and
- a cargo.

* * * * *

SEQUENCE LISTING

```
<160> NUMBER OF SEQ ID NOS: 3

<210> SEQ ID NO 1
<211> LENGTH: 35
<212> TYPE: PRT
<213> ORGANISM: artificial sequence
<220> FEATURE:
<223> OTHER INFORMATION: a dual-targeted therapeutic peptide for
      Nasopharyngeal carcinoma

<400> SEQUENCE: 1

Phe Ala Glu Lys Phe Lys Glu Ala Val Lys Asp Tyr Phe Ala Lys Phe
1               5                   10                  15

Trp Asp Gly Ser Gly Leu Thr Val Ser Pro Trp Tyr Leu Thr Val Ser
            20                  25                  30

Pro Trp Tyr
        35

<210> SEQ ID NO 2
<211> LENGTH: 18
<212> TYPE: PRT
<213> ORGANISM: artificial sequence
<220> FEATURE:
<223> OTHER INFORMATION: a targeted therapeutic peptide for
      nasopharyngeal carcinoma

<400> SEQUENCE: 2

Phe Ala Glu Lys Phe Lys Glu Ala Val Lys Asp Tyr Phe Ala Lys Phe
1               5                   10                  15

Trp Asp

<210> SEQ ID NO 3
<211> LENGTH: 14
<212> TYPE: PRT
<213> ORGANISM: artificial sequence
<220> FEATURE:
<223> OTHER INFORMATION: a targeted therapeutic peptide for
      nasopharyngeal carcinoma

<400> SEQUENCE: 3

Leu Thr Val Ser Pro Trp Tyr Leu Thr Val Ser Pro Trp Tyr
1               5                   10
```